United States Patent [19]

Froemel

[11] 4,011,538
[45] Mar. 8, 1977

[54] FLUID SENSOR
[75] Inventor: John G. Froemel, San Diego, Calif.
[73] Assignee: Illinois Tool Works Inc., Chicago, Ill.
[22] Filed: Jan. 30, 1976
[21] Appl. No.: 653,161
[52] U.S. Cl. .............................. 338/35; 23/254 E; 73/27 R
[51] Int. Cl.² .......................................... H01L 7/00
[58] Field of Search ......... 338/34, 35; 73/23, 27 R; 200/61.06, 61.04; 340/235; 23/254 E, 255 E, 232 E

[56] References Cited
UNITED STATES PATENTS

| | | | |
|---|---|---|---|
| 2,589,983 | 3/1952 | Blodgett et al. | 338/35 X |
| 2,806,991 | 9/1957 | White | 338/34 X |
| 3,479,257 | 11/1969 | Shaver | 23/254 E X |

Primary Examiner—C. L. Albritton
Attorney, Agent, or Firm—Glenn W. Bowen; Robert W. Beart

[57] ABSTRACT

A low-cost fluid sensor which has a controlled resistance value is provided by depositing a resistance material between two electrodes on a portion of a molecular sieve layer. A heating resistor for drying out the fluid sensor may also be provided by depositing a resistance strip over another portion of the molecular sieve layer, or alternately by providing the resistance strip adjacent the molecular sieve layer on a supporting substrate.

7 Claims, 3 Drawing Figures

FLUID SENSOR

BACKGROUND OF THE INVENTION

Prior fluid sensing devices have been proposed in which a pair of spaced-apart electrodes are supported on a surface layer. One type of such device for sensing humidity utilizes a hygroscopic substance, such as an ionic salt, which is applied to the surface between two conductive electrodes, but this type of sensor is easily damaged and is subject to contamination.

Another related type of prior fluid sensing device relies on the absorbed fluid on the surface between the electrodes. This type of device is unacceptable for many applications because it requires special measuring circuits due to the high surface resistivity of the insulating substrate.

The construction of a fluid sensor with two electrodes applied on a supporting surface is desirable, however, because of the resulting simplicity and low profile which is provided and the fact that the flat surface area of the substrate provides a large area for adsorption which increases the sensitivity of the device.

It is, therefore, the object of the present invention to provide a fluid sensing device in which a resistance of a predetermined value may be applied on a molecular sieve layer between two electrodes so as to make electrical contact therebetween.

It is a further object of the present invention to provide a fluid sensor in which a resistance path is formed on a molecular sieve substrate in a manner such that desirable properties of the layer may be utilized to advantage.

It is an additional object of the present invention to provide a fluid sensor that is made up of a molecular sieve layer, two spaced-apart electrodes and a resistance strip deposited on the molecular sieve layer between the two electrodes, and preferably also a heating resistor which is deposited on the molecular sieve layer, or is positioned in proximity thereto.

DESCRIPTION OF THE DRAWINGS

The present invention is illustrated by reference to the drawings in which.

TECHNICAL DESCRIPTION OF THE INVENTION

Figure 1:
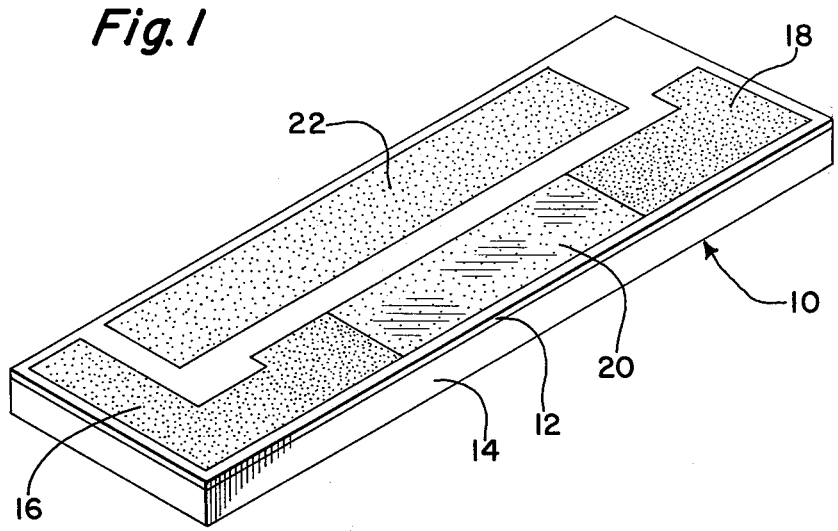
FIG. 1 is a perspective view of a fluid sensor constructed in accordance with the present invention which has a heating resistor deposited on the upper surface of said sensor.

The fluid sensor of the present invention is primarily intended as a humidity sensor and is illustrated in the drawings in which the reference numeral 10 generally indicates the sensor. The sensor 10 is constructed with a layer of a porous material 12 which is deposited on a suitable substrate layer 14 which is relatively much thicker than the porous layer 12 which may be an electrical insulating, heat-resistant material such as aluminum oxide. The porous layer 12 is made of a molecular sieve material which preferably is a synthetically-produced crystalline metal aluminosilicate that has been activated for adsorption by removing its water by hydration. Molecular sieve material of this type is commercially available from the Linde Division of the Union Carbide Corporation.

Molecular sieve materials have many advantages over other types of materials. They may adsorb water and may be cleared by heat in a reversible process, and they probably are the most efficient and selective adsorbent that is commercially available for the drying and purification of gases and liquids. In addition, these materials adsorb polar and polarizable molecules, such as water, with a tenacity that is not found with conventional adsorbents, and they are available in pellet, bead or powder form. Molecular sieve materials may withstand temperatures as high as 1100° F. with no effect on their crystallinity or adsorptive properties resulting. Moreover, molecular sieves do not shatter when they are contacted with liquid water, and they are not changed chemically during adsorption or disorption.

Physically, molecular sieves have a highly porous structure since about one-half of their volume is comprised of a series of inter-connected cavities. Pores or apertures of precisely uniform size selectively control the entrance of molecules into these cavities. While the efficiency of most adsorbents falls off sharply as the relative humidity drops, molecular sieves continue to perform satisfactorily under such conditions as their high adsorptive capacity remains fairly constant down to extremely low water concentrations.

The elongated rectangular shaped sensor 10 of the drawings provides a large, flat surface area which increases the sensitivity of the sensor, thus providing a sensitive and stable sensor for a wide range of conditions. The large surface molecular sieve layer 12 may be purchased in powder form, mixed with clay and a conventional binder and then extruded onto the substrate layer 14. It is next dried, screened, or cut, and then fired to drive out the water of hydration so as to "activate" the molecular sieves, or make them readily adsorbent.

The electrodes 16, 18 are formed of a conductive material which is preferably a platinum-silver alloy that is deposited by sputtering, vacuum evaporation, or other suitable means, on the molecular sieve layer 12 — although alternately they could be applied on the substrate 14. The preferred molecular sieve structure consists of a tetrahedron of four oxygen ions which surround a smaller silicon or aluminum cation. The positive charge deficiency in the alumina tetrahedra is made up by cations. Each oxygen anion is shared with another silica or alumina tetrahedron so that the crystal lattice is extended in a three-dimensional manner. The resulting crystal is honey-combed with relatively large cavities, each of which are connected with six adjacent cavities through openings or pores and the initial water of hydration is held in these cavities. Because of the open, highly-porous structure of the molecular sieve layer 12, the electrode material for the electrodes 16, 18 preferably extends into pores of the crystal structure of the molecular sieve layer 12 where it is deposited thereon.

The molecular sieve layer 12 is capable of withstanding high temperatures and the substrate 14 is also desirably made of a substance, such as aluminum oxide, which is capable of withstanding high temperatures, and if a platinum-silver alloy is used for the electrodes 16, 18, they also will not deteriorate at high temperatures. It is highly advantageous, therefore, to have all of the components of the sensor capable of functioning at high temperatures.

In order to reduce the surface resistivity of the fluid sensor 10 and to provide an output resistance of a controlled value so as to simplify the external measuring circuit required, a resistance layer 20 is deposited between the electrodes 16 and 18. The resistance layer 20 is preferably formed of a cermet material, which is an alloy of a heat-resistant compound such as titanium carbide and conductive metal such as nickel. Like the electrodes 16, 18, the resistance layer 20 may be sputtered, vacuum evaporated or deposited by other suitable means onto the substrate 12 so that it also permeates into the porous molecular sieve layer 12.

The temperature range of operation of the sensor 10 of present invention should be from approximately −55° C. to 90° C, and it is anticipated that it will be useful for sensing humidity over the range of at least three to two hundred fifty grains of moisture per pound of dry air. The output impedance, while controllable, may still be on the order of 10,000 ohms, or more, in order to reduce power dissipation.

The sensor 10 may be "cleared" after it has absorbed water, or other fluid, by application of heat or by blowing of dry hot air over it in order to eliminate the fluid that has been absorbed. One way of accomplishing this is by a heating resistor 22 as shown in FIG. 1. The heating strip may be sputtered onto the layer 12 so that an electrical current flowing through the heating resistor 22 will serve to dry out the sensor. The heating resistor 22 is preferably applied by the same means and at the same time as the resistance layer 20. It preferably is formed of a platinum-silver alloy or a palladium-silver alloy.

Figure 2:
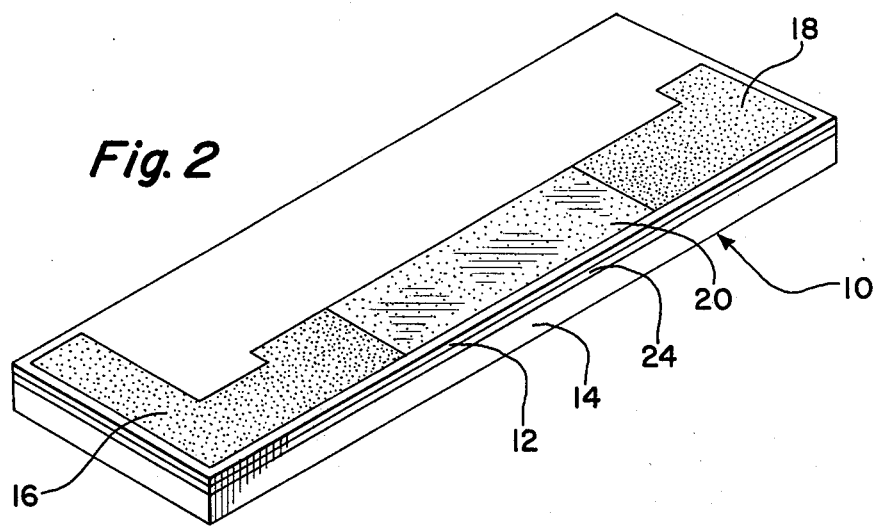
FIG. 2 is a fluid sensor in accordance with the present invention in which a heating resistor is provided between a fluid sensing layer and a substrate layer.
Figure 3:
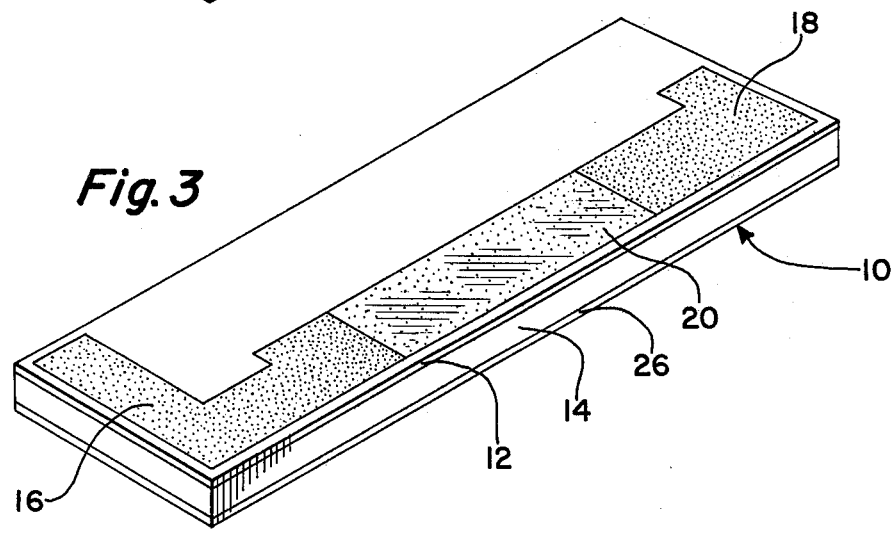
FIG. 3 is a perspective view of a fluid sensor constructed in accordance with the present invention in which a heating layer is applied to the bottom of a substrate which supports the fluid sensing layer.

The heating resistor 22 may also be provided on the substrate 14 between the substrate 14 and the molecular sieve layer 12, as shown by the layer 24 of FIG. 2; or on the bottom of the substrate 14, as shown by the layer 26 of FIG. 3. The heating time required to clear the sensor preferably will be on the order of 5 to 7 seconds while the response time of the sensor will generally be on the order of a maximum of ten seconds. If a faster response time is desired, the substrate layer 14 may be made of a polyamide or other low heat capacity material.

What is claimed is:

1. A fluid sensor comprising a molecular sieve layer, first and second spaced-apart electrodes and a resistance material deposited on said layer so as to make an electrical connection between said first and second electrodes.

2. A fluid sensor as claimed in claim 1 further comprising a heating resistor.

3. A fluid sensor as claimed in claim 2 further comprising a supporting substrate for said layer wherein said electrodes, said substrate and said heating resistor are all formed of heat-resistance compositions.

4. A fluid sensor as claimed in claim 2 wherein said heating resistor is deposited on a portion of said layer.

5. A fluid sensor as claimed in claim 3 wherein said heating resistor is disposed intermediate said layer and said supporting substrate.

6. A fluid sensor as claimed in claim 3 wherein said heating resistor is disposed on a different surface of said supporting substrate than is said molecular sieve layer.

7. A fluid sensor as claimed in claim 1 wherein said fluid sensor is a humidity sensor.

* * * * *